United States Patent [19]

Okada

[11] Patent Number: 5,390,662
[45] Date of Patent: Feb. 21, 1995

[54] ELECTRONIC ENDOSCOPE APPARATUS USING CIRCUIT BOARD HAVING CAVITY

[75] Inventor: Fujio Okada, Omiya, Japan

[73] Assignee: Fuji Photo Optical Co., Ltd., Omiya, Japan

[21] Appl. No.: 20,797

[22] Filed: Feb. 22, 1993

[30] Foreign Application Priority Data

Mar. 2, 1992 [JP] Japan .................. 4-081662

[51] Int. Cl.6 ............................................. A61B 1/04
[52] U.S. Cl. ............................................. 128/4; 128/6
[58] Field of Search ............... 128/4, 6; 361/760, 761, 361/764; 377/12; 358/98

[56] References Cited

U.S. PATENT DOCUMENTS 4,732,446 3/1988 Gipson et al. .................. 361/764 X
4,853,772 8/1989 Kikuchi ............................ 128/6 X

FOREIGN PATENT DOCUMENTS 8802210 3/1988 WIPO .

Primary Examiner—Richard J. Apley
Assistant Examiner—John P. Leubecker
Attorney, Agent, or Firm—Oliff & Berridge

[57] ABSTRACT

An electronic endoscope apparatus uses a circuit board having a cavity for achieving a predetermined electrical insulation. The apparatus includes a patient circuit on the side of the electronic endoscope, an output circuit for performing a predetermined image processing, and an isolation device for maintaining a predetermined dielectric strength between the two circuits; and the cavity is formed on one circuit board where the isolation device is disposed extending over the cavity. Further, the cavity is extended outward by a predetermined length so that signal lines on the two sides to be connected to the isolation device are positioned with a distance from each other on the circuit board by which a predetermined dielectric strength may be maintained. Thereby, current detouring through the circuit board may be effectively prevented and it is possible to isolate the patient circuit and the output circuit from each other also on the circuit board.

2 Claims, 3 Drawing Sheets

ELECTRONIC ENDOSCOPE APPARATUS USING CIRCUIT BOARD HAVING CAVITY

BACKGROUND OF THE INVENTION

This application claims the priority of Japanese Patent Application No. 4-81662, filed on Mar. 2, 1992, which is incorporated herein by reference.

1. Field of the Invention

The present invention relates to electronic endoscope apparatus using a circuit board having a cavity and, more particularly, relates to the circuit construction for electrically isolating a patient circuit on the electronic endoscope side from an output circuit.

2. Description of the Related Art

An electronic endoscope apparatus is conventionally known, for observing the interior of a body cavity such as the alimentary canal by means of CCD (Charge Coupled Device) provided at the terminal end thereof to form a solid image pickup device. In this type of electronic endoscope apparatus, an internal image of the subject to be observed (patient) picked up by the above CCD may be captured by inserting the electronic endoscope (electronic scope) into the body cavity, whereby such as examination and diagnosis may be conducted while observing the image displayed on a monitor.

FIG. 4 schematically shows the construction of an electronic endoscope apparatus of this type. This apparatus is constructed to have an electronic endoscope which is connected to an external processor unit. As shown in the figure, a patient circuit 2 is disposed on the circuit board 1 in the electronic endoscope apparatus in such a manner that it is connected to an output circuit (secondary circuit) 4 via an isolation device 3. Specifically, the patient circuit 2 and the output circuit 4 include such components as: the above CCD; CCD driver; a signal processing circuit for performing image processing such as gamma-correction with respect to the video signal obtained at the CCD; A/D converter; D/A converter; and a memory; and the isolation device 3 is placed at one of the in-between positions in the course of these circuits. Accordingly, those circuits toward the electronic endoscope from the isolation device 3 constitute the patient circuit 2 while the circuits on the external processor unit side or the monitor side constitute the output circuit 4. Here, a photocoupler or a pulse transformer for example is used as the isolation device 3 so as to maintain a dielectric strength of 3~4 kV or more by the isolation device 3, thereby securing the safety of the electronic endoscope for the patient.

In the above conventional electronic endoscope apparatus, however, though as described a predetermined electrical insulation at the signal transmission lines is maintained by the isolation device 3, it is possible that a current flows to the patient circuit 2 from the output circuit 4 in a manner of detouring around through the circuit board 1, causing a problem that the dielectric strength is not completely maintained. In other words, as indicated by chain line 100 in FIG. 4, a flow passage of current to the wiring portion of the patient circuit 2 from the wiring portion on the side of the output circuit 4 is formed through the circuit board 1 at the outside of the attaching portion of the isolation device 3, whereby isolation of the patient circuit from the output circuit by the isolation device 3 does not make sense.

An arrangement may be taken into consideration to maintain the dielectric strength at the circuit board 1, in which the distance on the circuit board 1 between the patient circuit 2 and the output circuit 4 is increased in the state where the isolation device 3 is floated (isolated for example by an insulating material) from the circuit board 1. In such a case, however, the circuit board 1 itself becomes larger and more complicated in construction, resulting in a disadvantage that the size of the apparatus is increased.

SUMMARY OF THE INVENTION

In view of the above problems, it is an object of the present invention to provide an electronic endoscope apparatus using a circuit board having a cavity in which failure in providing a predetermined electrical insulation caused by the circuit board may be effectively and simply prevented and at the same time a reduction in the space for the circuit board is possible.

To achieve the above object, an electronic endoscope apparatus using a circuit board having a cavity is provided in accordance with the present invention, including: a patient circuit on the side of an electronic endoscope to be applied on the subject for observation; an output circuit for performing a predetermined image processing with respect to a video signal; and an isolation device connected between the patient circuit and the output circuit to maintain a predetermined dielectric strength thereat, and characterized in that a cavity for maintaining a predetermined dielectric strength is formed on one circuit board at the connecting portion between the patient circuit and the output circuit and said isolation device is disposed to be extended over the cavity.

Further, the above cavity is preferably formed to be extended outward by a predetermined length such that the signal lines on the two sides to be connected to the isolation device are disposed with a distance on the circuit board therebetween capable of maintaining a predetermined dielectric strength.

According to the above construction, the current detouring around through the circuit board may be effectively prevented by the cavity formed on the circuit board, thereby the patient circuit and the output circuit are electrically isolated from each other not only at their signal lines but also in a manner including the circuit board.

DESCRIPTION OF THE PREFERRED EMBODIMENT

Figure 1:
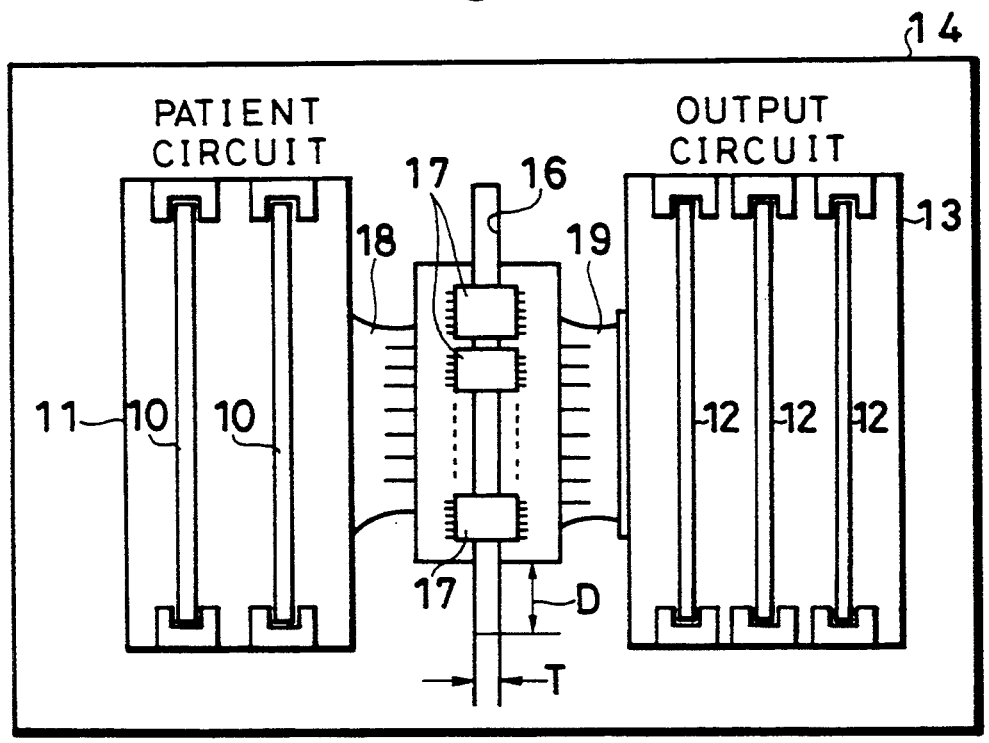
FIG. 1 shows the construction in an external processor unit of an electronic endoscope apparatus according to an embodiment of the present invention.
Figure 2:
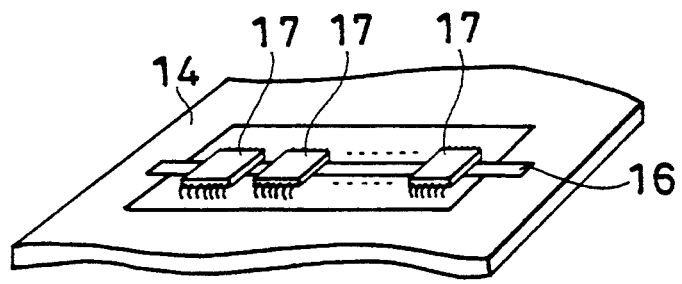
FIG. 2 is a perspective view of the connecting portion of an isolation device in the embodiment.

FIG. 1 shows the construction in the external processor unit of the electronic endoscope apparatus according to an embodiment of the present invention, and FIG. 2 shows a perspective view of the connecting portion of an isolation device thereof. Referring to FIG. 1, substrates 10 for the patient circuit side having thereon the components for constituting the patient circuit mounted are retained at an accommodation portion 11, while substrates 12 for the output circuit side having thereon the components for constituting the output (secondary) circuit mounted are retained at an accommodation portion 13. These substrates 10, 12 are connected to one circuit board 14 such as by connectors positioned at their side surface portion. Here, a longitudinally elongated cavity 16 is formed on the circuit board 14 between the patient circuit and the output circuit, where an isolation device 17 is provided in a manner extended over the cavity 16. The patient circuit side substrate 10 is connected through signal line 18 to the isolation device 17, while the output side substrate 12 is connected thereto through signal line 19.

In this embodiment, the above cavity 16 is formed to have its width "T" of for example about 4 mm and to be extended to about D=20 mm outward from the attaching portion of the isolation device 17. Thus, the dielectric breakdown strength of the cavity 16 is about 1 kV/1 mm and a dielectric strength of about 4 kV is secured by the width of the above 4 mm. Further the circuit board 14 is formed of a resin material, which has a dielectric breakdown strength of about 0.1 kV/1 mm. A dielectric strength of about 4 kV is thereby maintained also at the circuit board around the cavity, since about 40 [20(=D)×2] mm is provided at the outside of the isolation device from the signal line 18 on the patient circuit side to the signal line 19 on the output circuit side.

While in this embodiment a photocoupler is used as the above isolation device 17, it is also possible to use a pulse transformer. In the case of a photocoupler, the patient circuit and the output circuit, after converting an electrical signal into a luminous signal, may be electrically isolated from each by returning it further into an electrical signal, while, in the case of a pulse transformer, the above two may be electrically isolated from each other by the withstand voltage characteristic of the transformer.

Figure 3:
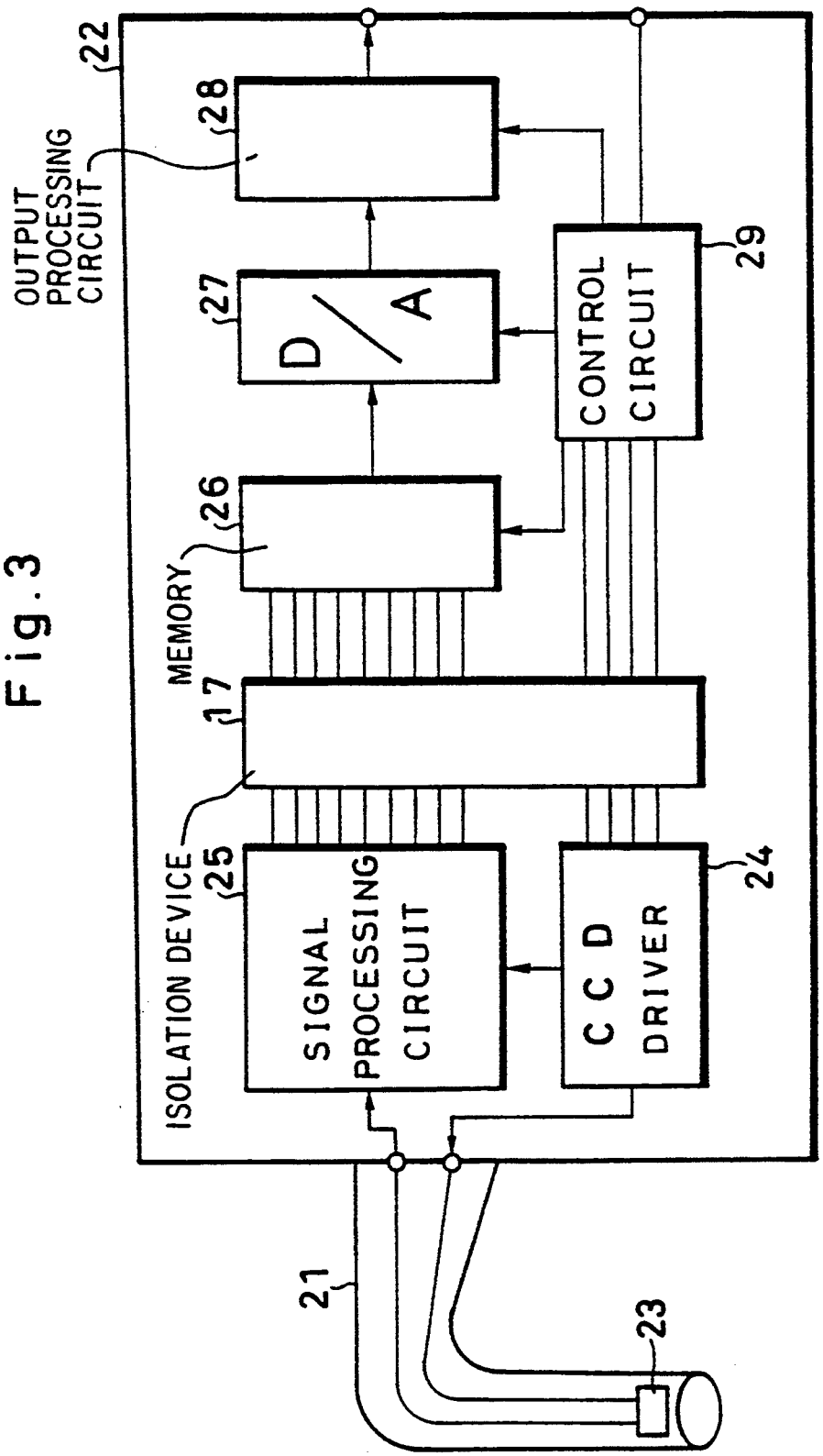
FIG. 3 is a block diagram showing specifically the circuit construction of the electronic endoscope apparatus of the embodiment.
Figure 4:
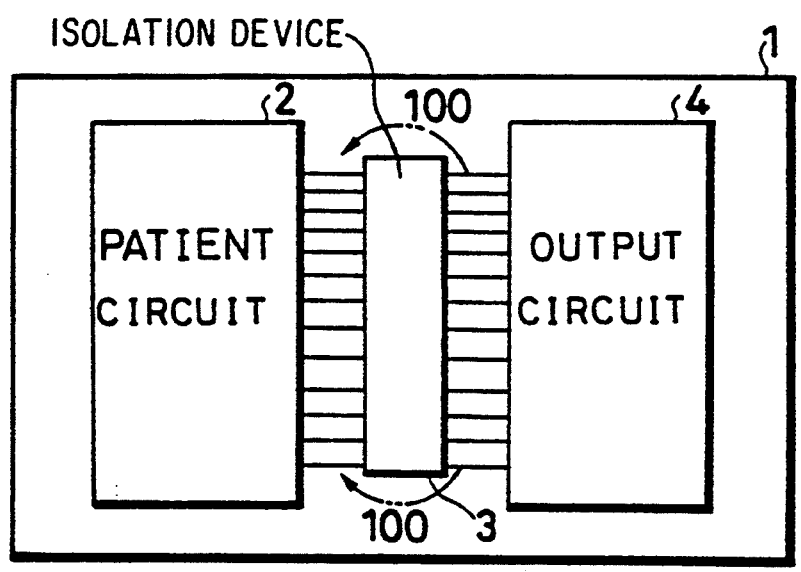
FIG. 4 is a diagram showing the connection of an isolation device in a conventional example.

FIG. 3 shows a specific example of the circuitry within the above electronic endoscope apparatus. In the electronic endoscope apparatus, as shown in the figure, an electronic endoscope (electronic scope) 21 constituting the scope is connected through connectors to an external processor unit 22. A solid pickup device (CCD) 23 is provided at the distal end of the electronic endoscope 21 in a manner linked with the observation window, so that an internal image of the subject to be observed is picked up by the CCD 23 when irradiating a light through an irradiation window (not shown).

On the other hand, CCD driver 24 for driving the above CCD 23 and a signal processing circuit 25 for processing such as A/D conversion, sampling processing, and gamma-correction with respect to a video signal obtained at CCD 23 are provided on the external processor unit 22, and these circuits including the CCD 23 constitute the patient circuit. Further, provided thereon via the isolation device 17 are a frame memory 26, D/A converter 27, an output processing circuit 28, and a control circuit 29. Accordingly, while control signal is output to such as the CCD driver 24 on the side of the patient circuit from the control circuit 29 through the isolation device 17, video signal is supplied from the signal processing unit 25 to the memory 26 on the side of the output circuit through the isolation device 17. It should be noted that, in addition to these, such as a light source and its control circuit are provided on the side of the output circuit.

According to the construction of the above described embodiment, the output circuit side and the patient circuit are electrically isolated from each other by the isolation device 17 at their signal transmission lines. Furthermore, it is possible to maintain a dielectric strength of about 4 kV at the circuit board 14 between the patient circuit and the output circuit by the presence of the cavity 16 on the circuit board 14 as shown in FIG. 1, thereby the patient circuit may be electrically isolated completely from the output circuit.

As has been described, according to the present invention, a detouring of current through the circuit board may be effectively prevented and, comparing to the construction where the isolation device is caused to float from the circuit board for example by an insulating material, the circuit board itself may be reduced in size to prevent an increase in the size of the apparatus.

In the above described embodiment, a case has been shown where the cavity 16 is formed on one circuit board 14 on which the patient circuit and the output circuit are mounted. However, various constructions such as mounting a part of the patient circuit or the output circuit thereon may be considered for the circuit board 14 and the above cavity 16 may be formed on all the circuit boards where an isolation device is provided at the connecting portion between the patient circuit and the output circuit.

Further, while in the above described embodiment a case has been shown where the CCD driver 24 and the signal processing circuit 25 forming the patient circuit are disposed in the external processor unit 22, it is also possible to dispose these circuits on the electronic endoscope 21 where the circuit board 14 having the isolation device 17 on the cavity 16 thereof is provided in the vicinity of the connector on the side of the external processor unit 22 or in the vicinity of the connector on the side of the electronic endoscope 21.

What is claimed is:

1. An electronic endoscope apparatus, comprising:
a low voltage patient circuit on a side of an electronic endoscope to be applied on a subject for observation;
a low voltage output circuit for performing a predetermined image processing with respect to a video signal; and
current flow prevention means for preventing unwanted current flow in or on a circuit board between the patient circuit and the output circuit, comprising;
an isolation device connected between the patient circuit and the output circuit to maintain a predetermined dielectric strength, and
a cavity for maintaining a predetermined dielectric strength formed on the circuit board at a connecting portion between the patient circuit and the output circuit, the cavity extending outwardly from an attaching portion of the isolation device by a predetermined length such that signal lines on the two sides to be connected to the isolation device are disposed with a distance along the circuit board therebetween capable of maintaining a predetermined dielectric strength, wherein a width of the cavity is at least 4 millimeters and the predetermined length is at least 20 millimeters;
said isolation device extending over the cavity.

2. An electronic endoscope apparatus according to claim 1, wherein a photocoupler or a pulse transformer is used as said isolation device.

* * * * *